(12) United States Patent
Umemura

(10) Patent No.: US 7,269,994 B2
(45) Date of Patent: Sep. 18, 2007

(54) CHROMATOGRAPH/MASS SPECTROMETER

(75) Inventor: Yoshikatsu Umemura, Osaka-fu (JP)

(73) Assignee: Shimadzu Corporation, Kyoto (JP)

( * ) Notice: Subject to any disclaimer, the term of this patent is extended or adjusted under 35 U.S.C. 154(b) by 66 days.

(21) Appl. No.: 11/272,071

(22) Filed: Nov. 14, 2005

(65) Prior Publication Data

US 2006/0101898 A1    May 18, 2006

(30) Foreign Application Priority Data

Nov. 18, 2004   (JP) ............... 2004-334150

(51) Int. Cl.
  *G01N 30/86* (2006.01)
  *G01N 30/72* (2006.01)
  *G01N 30/02* (2006.01)

(52) U.S. Cl. ............ 73/23.37; 73/23.35; 73/61.52; 95/82; 96/101; 210/656; 422/70; 422/89; 436/161

(58) Field of Classification Search ............. 73/23.37, 73/61.58, 23.35, 61.52; 95/82; 96/101; 210/656; 422/70, 89; 436/161
See application file for complete search history.

(56) References Cited

U.S. PATENT DOCUMENTS 6,329,652 B1 * 12/2001 Windig et al. ............. 250/282
6,438,499 B1 * 8/2002 Hayashi ..................... 702/30
6,641,783 B1    11/2003 Pidgeon et al.
2003/0113936 A1   6/2003 Yamamoto
2004/0126277 A1   7/2004 Yamamoto

FOREIGN PATENT DOCUMENTS

JP    2004-198123    7/2004

OTHER PUBLICATIONS

European Search Report dated Feb. 7, 2006, of corresponding European Application No. EP 05 02 4583.

* cited by examiner

*Primary Examiner*—Daniel S. Larkin
(74) *Attorney, Agent, or Firm*—Westerman, Hattori, Daniels & Adrian, LLP.

(57) ABSTRACT

The present invention provides a chromatograph/mass spectrometer capable of producing a composite chromatogram from plural chromatogram signals without causing the baseline level to rise or the intensity of the chromatogram peak to decrease. The chromatograph/mass spectrometer includes a chromatograph unit for separating a sample into components in the order of time, a mass spectrometer unit for analyzing the components of the sample, and a signal generator for producing a signal carrying a chromatogram obtained by the analysis. It also includes a chromatogram composer for receiving signals of plural chromatograms simultaneously measured under different conditions, for choosing the largest value of the plural signals for each point in time, and for integrating the chosen values to produce a composite chromatogram.

1 Claim, 2 Drawing Sheets

CHROMATOGRAPH/MASS SPECTROMETER

The present invention relates to a chromatograph/mass spectrometer and particularly to one having a function for producing an analogue or digital signal carrying a chromatogram obtained through a measurement.

BACKGROUND OF THE INVENTION

A chromatograph/mass spectrometer is an apparatus for creating a chromatogram of a sample. It includes a chromatograph unit (e.g. a gas chromatograph or a liquid chromatograph) for separating the sample into components in the order of time, and a mass spectrometer unit for detecting one or more components each having a specified mass number (i.e. mass-to-charge ratio). The chromatogram may be converted into an analogue or digital signal and supplied to a fraction collector which separately collects each component (for example, see paragraphs 0002 to 0005 and FIG. 4 of the Japanese Unexamined Patent Publication No. 2004-198123) or a similar device. Any device that uses chromatogram signals has one or more parameters relating to the use of the supplied signal for specific operations, so that these parameters should be correctly determined for the signal to be properly used.

There are many types of mass spectrometers that are capable of simultaneously observing plural chromatograms under different conditions. For example, they may be chromatograms of plural kinds of ions monitored under an SIM (Selected Ion Monitoring) measurement, or plural mass chromatograms obtained through a scanning measurement. To send plural chromatograms simultaneously obtained under different conditions to another apparatus requires a special technique if there is only one analogue or digital output port available. For example, some conventional chromatograph/mass spectrometers add or average the plural signals to produce a single composite signal.

The composite signal produced through the adding operation is accompanied by the following problems: In general, each chromatogram peak corresponding to each component of the sample appears on only one or a few chromatograms before the adding operation, as shown in FIG. 3, of the instant application. Therefore, the peak intensity never changes even if the number of the signals added is increased. However, the baseline, which corresponds to the noise contained in the signal, becomes higher because the adding operation multiplies the level of the baseline by the number of the signals added together. If there is a peak having a large intensity as in the first chromatogram in FIG. 3, the adding operation may make the peak signal saturated as shown by the circle P, which results in the resultant composite signal having an incorrect waveform.

In contrast, the averaging operation doesn't significantly change the level of the baseline, as shown in FIG. 4, of the instant application. However, this operation divides the intensity of the chromatogram peak by the number of the signals used, thereby making the peak shorter.

To avoid these problems, the operator of the conventional mass spectrometer needs to take the trouble to appropriately change the parameter setting of the fraction collector or other apparatuses that use chromatogram signals whenever the number of the signals used is changed. Taking this problem into account, the present invention intends to provide a new chromatograph/mass spectrometer, which neither raises the level of the baseline nor reduces the height of the chromatograph peak through the composition process, and in which a change in the condition or the number of the signals to be used in the composition process doesn't require the operator to change the parameter setting of apparatuses that use chromatogram signals produced by the mass spectrometer.

SUMMARY OF THE INVENTION

Thus, the present invention provides a chromatograph/mass spectrometer having a chromatograph unit for separating a sample into components in the order of time, a mass spectrometer unit for analyzing the components of the sample, and a signal generator for producing a signal carrying a chromatogram obtained by the analysis, which further includes a chromatogram composer for receiving signals of plural chromatograms simultaneously measured under different conditions, for choosing the largest value of the plural signals for each point in time, and for integrating the chosen values to produce a composite chromatogram.

The above-described construction prevents the baseline level or the peak intensity of the resultant composite chromatogram from being significantly influenced by a change in the condition of the analysis performed by the mass spectrometer. The operator no longer needs to frequently change the setting of apparatuses that use chromatogram signals produced by the mass spectrometer unit. Thus, the efficiency of the condition-setting work for the apparatuses used in the analysis is improved.

DETAILED DESCRIPTION OF A PREFERRED EMBODIMENT

Figure 1:
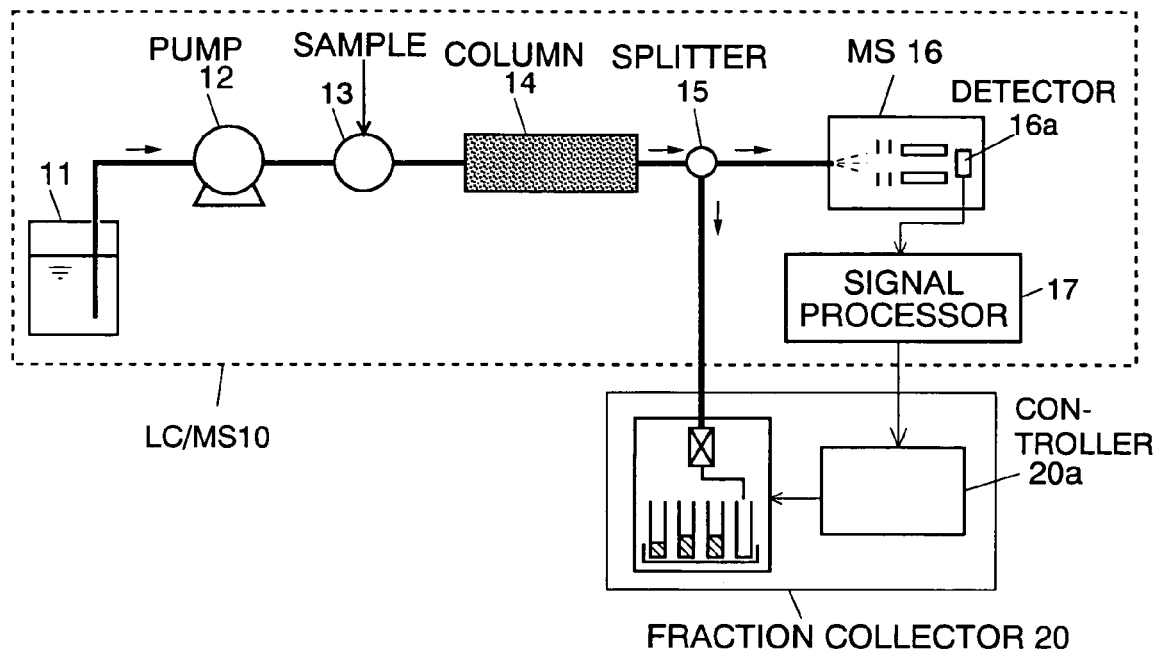
FIG. 1 is a block diagram showing the construction of the main elements of a liquid chromatograph/mass spectrometer as an embodiment of the present invention.

FIG. 1 shows the construction of the main elements of a liquid chromatograph/mass spectrometer (LC/MS) as an embodiment of the present invention. In the present embodiment, the liquid chromatograph/mass spectrometer 10 supplies the fraction collector 20 with a chromatogram signal obtained by mass analysis. The fraction collector 20 separately collects each component of the sample according to the signal supplied.

The mobile phase container 11 contains a mobile phase, which is siphoned by the pump 12 and supplied through the sample-introducing section 13 into the column 14 at a constant rate. At the sample-introducing section 13, a liquid sample is injected into the mobile phase, which carries the sample into the column 14. While passing through the column 14, the liquid sample is separated into components in the order of time, and finally exits the column 14 as elution. This elution is split by the splitter 15 into two channels leading to the mass spectrometer unit 16 and the fraction collector 20, respectively. The dimensions of the piping and other elements are determined so that the time required for the sample to flow from the splitter 15 to the fraction collector 20 is longer than that required for the same sample to flow from the splitter 15 to the mass spectrometer unit 16. This design enables the fraction collector 20 to operate according to the chromatogram obtained by the mass spectrometer unit 16. The signal processor 17 creates a chromatogram from the detection signal received from the detector 16a of the mass spectrometer unit 16. It also produces a composite chromatogram from plural chromatograms according to necessity. This composition process will be detailed later.

The chromatogram signal produced by the signal processor 17 is fed to the controller 20a of the fraction collector 20. According to the peaks appearing on the chromatogram, the fraction collector 20 operates an electromagnetic valve and an arm so as to collect plural samples of the elution, each containing a different component, and introduce each sample into separate vials. In general, a chromatogram peak is recognized by analyzing the baseline level, the peak intensity, the gradient on the rising side of the peak, and other characteristic values. For this analysis, the operator should preset necessary parameters of the fraction collector 20, such as the thresholds for the aforementioned characteristic values.

Figure 2:
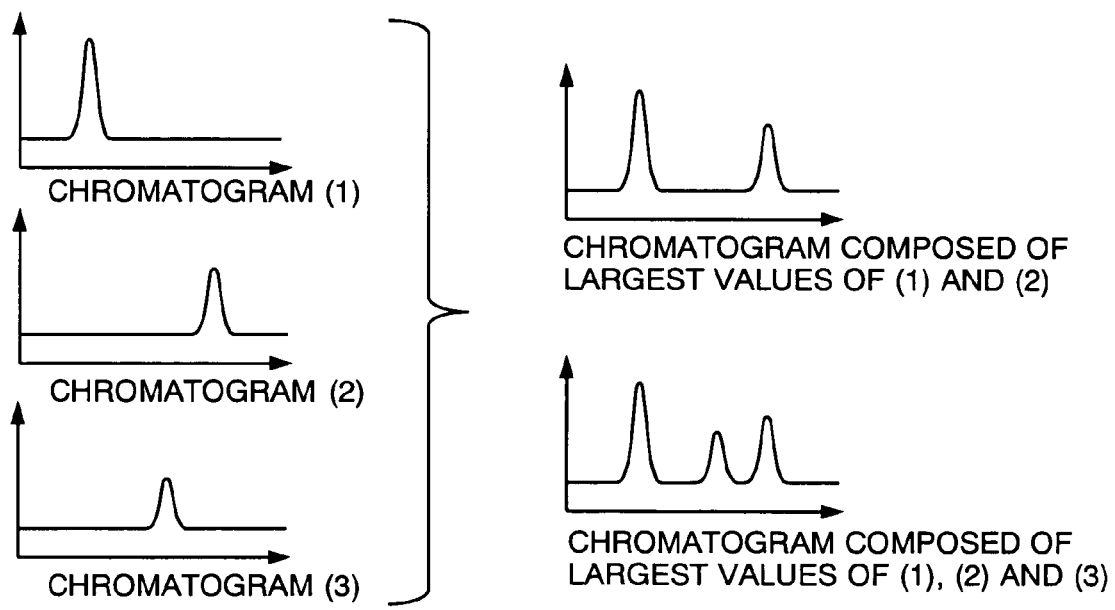
FIG. 2 is a diagram illustrating the method of producing a composite chromatogram in the chromatograph/mass spectrometer according to the present invention.
Figure 3:
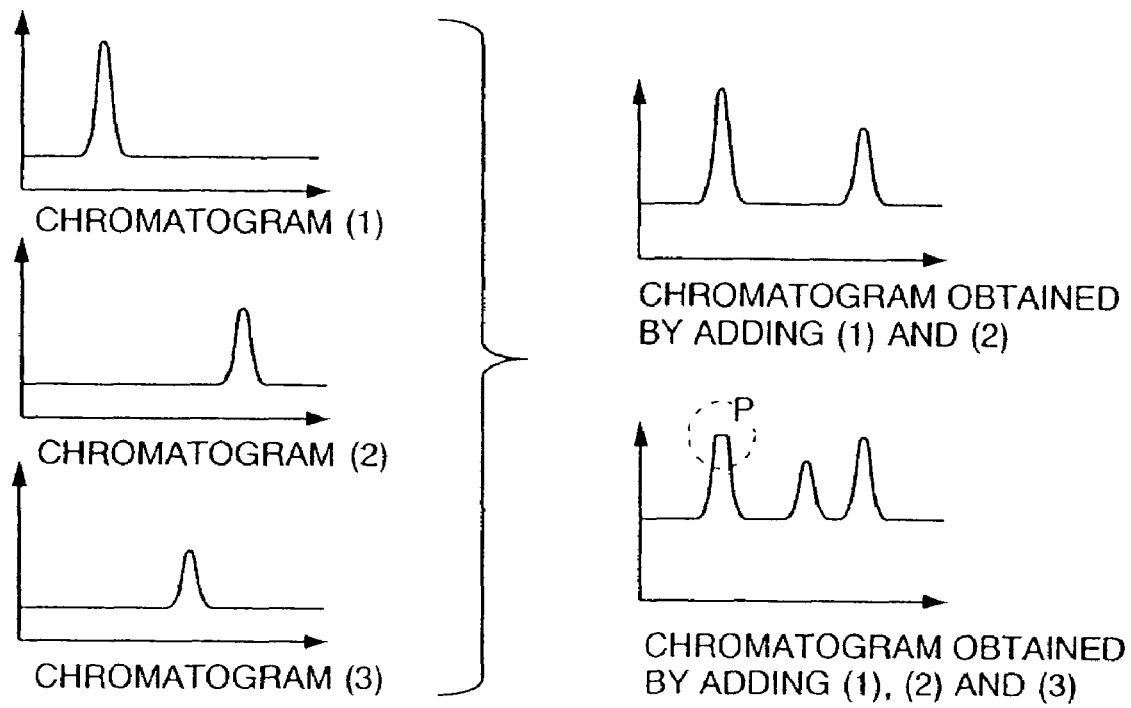
FIG. 3 is a diagram illustrating the method of producing a composite chromatogram by adding signals in a conventional chromatograph/mass spectrometer.
Figure 4:
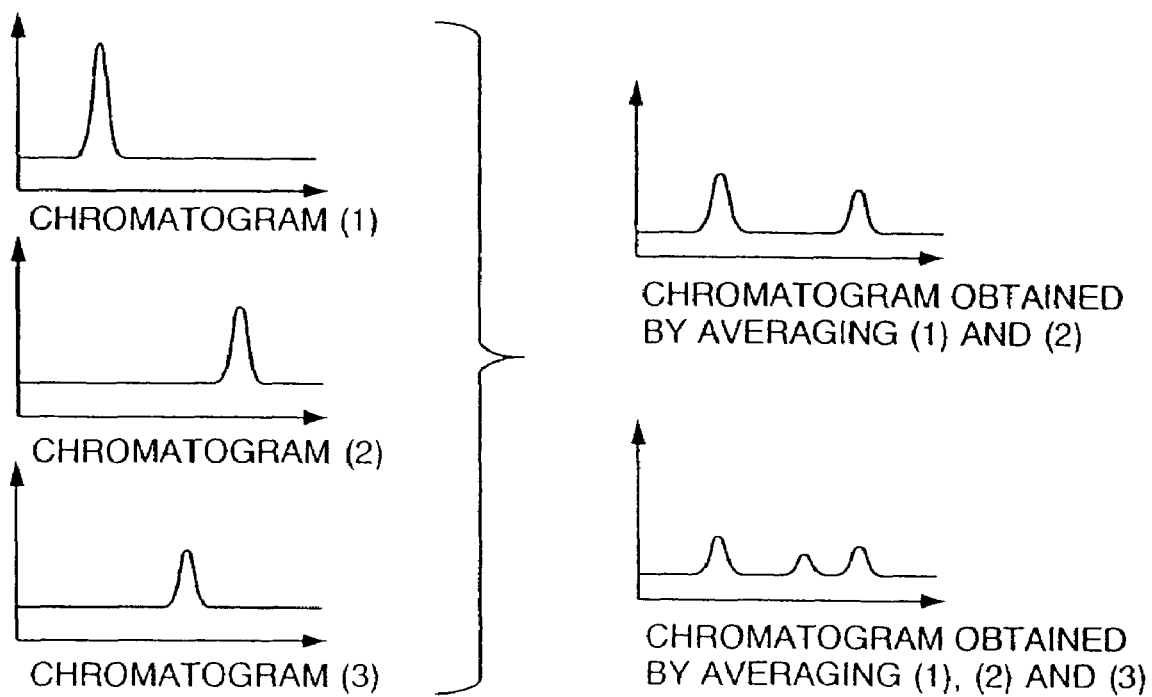
FIG. 4 is a diagram illustrating the method of producing a composite chromatogram by averaging signals in a conventional chromatograph/mass spectrometer.

The method of producing a composite chromatogram from plural chromatogram signals simultaneously obtained under different conditions in the chromatograph/mass spectrometer according to the present invention is described. Suppose that the mass spectrometer unit 16 is operated to perform an SIM measurement in which the intensity of three kinds of ions is monitored. The measurement result is shown in FIG. 2 as chromatograms 1, 2 and 3. According to the present method, the ion intensity of each chromatogram is converted into digital values with an A/D converter (not shown). Then, at each point in time, the signals of the three chromatograms are compared with each other, and the largest value is chosen to be supplied to the fraction collector 20 as a signal of the composite chromatogram. This composite chromatogram may be sent to the fraction collector 20 in the digitized form or converted back into an analogue signal before being sent to the fraction collector 20.

As shown in FIG. 2, the above-described method of producing a composite chromatogram never causes significant differences in the baseline level, the peak intensity and the peak shape (including the leading edge of the peak) between the original chromatograms and the resultant one. It also prevents the saturation of the resultant signal, which possibly occurs if the composite chromatogram is produced by the adding operation. Therefore, it is unnecessary to change the parameters of the fraction collector 20 even if the number of the original chromatograms to be used in the composition process is changed.

The chromatograph/mass spectrometer according to the present invention may be preferably constructed so that the operator is allowed to optionally choose the conventional adding or averaging method to produce a composite chromatogram instead of the above-described method in which the largest value is chosen.

The description thus far has focused on the case where three chromatograms obtained by monitoring three kinds of ions through an SIM measurement. It should be noted that the present invention can be applied to any other case in which the number and/or the type of the chromatograms is different. For example, the chromatogram may be a mass chromatogram, a multi ion chromatogram (MIC) or a total ion chromatogram (TIC) obtained through a scanning measurement. Moreover, the present invention can be used to produce a composite chromatogram from various types of chromatograms, including not only those obtained by a normal MS analysis but also those obtained by an MS/MS or MS" analysis, and also a combination of plural chromatograms obtained according to different values of ionization polarity.

The above-described embodiment is a mere example of the chromatograph/mass spectrometer according to the present invention. It is possible to embody the present invention in various forms within the spirit and scope thereof. For example, the apparatus to be connected to the chromatograph/mass spectrometer of the present invention is not limited to a fraction collector but can be any type of apparatus that uses the chromatogram signal produced by the chromatograph/mass spectrometer. The present invention can be also applied to a gas chromatograph/mass spectrometer instead of a liquid chromatograph/mass spectrometer as in the above-described embodiment.

What is claimed is:

1. A chromatograph/mass spectrometer having a chromatograph unit for separating a sample into components in an order of time, a mass spectrometer unit for analyzing the components of the sample, and a signal generator for producing a signal carrying a chromatogram obtained by the analysis, which further comprises a chromatogram composer for receiving signals of plural chromatograms simultaneously measured under different conditions, for choosing a largest value of the plural signals for each point in time, and for integrating the chosen values to produce a composite chromatogram.

* * * * *